(12) United States Patent
Chtourou et al.

(10) Patent No.: US 6,967,239 B1
(45) Date of Patent: Nov. 22, 2005

(54) METHOD OF FILTERING VIRUSES FROM A FACTOR VIII SOLUTION

(75) Inventors: Abdessatar Chtourou, Elancourt (FR); Michel Nogre, Vanves (FR); Pierre Porte, Les-Corbeil (FR)

(73) Assignee: Laboratoire Francias du Franctionnement et des Biotechnologies, Les Ulis (FR)

( * ) Notice: Subject to any disclaimer, the term of this patent is extended or adjusted under 35 U.S.C. 154(b) by 0 days.

(21) Appl. No.: 09/581,398

(22) PCT Filed: Dec. 14, 1998

(86) PCT No.: PCT/FR98/02715

§ 371 (c)(1),
(2), (4) Date: Aug. 3, 2000

(87) PCT Pub. No.: WO99/31138

PCT Pub. Date: Jun. 24, 1999

(30) Foreign Application Priority Data

Dec. 15, 1997 (FR) .................................. 97 15888

(51) Int. Cl.[7] .......................... A61K 35/14; A23J 1/00; C12N 7/04
(52) U.S. Cl. ................. 530/383; 530/384; 530/412; 530/414; 530/415; 530/416; 530/417; 530/418; 530/419; 530/420; 530/422; 530/427; 530/830; 530/831; 435/236; 435/238; 435/239; 514/802; 514/834
(58) Field of Search ................ 530/383, 384, 530/412, 414, 415, 416, 417, 418, 419, 420, 530/422, 427, 830, 831; 435/236, 238, 239; 514/802, 834

(56) References Cited

U.S. PATENT DOCUMENTS 4,758,657 A * 7/1988 Farb et al. ................ 530/383
5,371,195 A * 12/1994 Grandgeorge et al. ...... 530/383
5,677,162 A * 10/1997 Zou et al. .................. 435/124
5,869,617 A    2/1999 Fischer et al. ............. 530/381
5,892,005 A    4/1999 Fischer et al. ............. 530/413

FOREIGN PATENT DOCUMENTS

| EP | 197 554 | 10/1986 |
| EP | 383 645 | 8/1991 |
| EP | 468 181 | 1/1992 |
| WO | 91/18017 | 11/1991 |
| WO | 96/00237 | 1/1996 |
| WO | WO 96/00237 | * 1/1996 |
| WO | WO 98/37086 | * 8/1998 |

OTHER PUBLICATIONS

Josic et al., J. Chromatogr. B. Biomed. Appl., vol. 662, No. 2, pp. 181-190, 1994.*
BMM Process Filter, *PLANOVA*™, Validatable Virus Removable Filters, Asahi Chemical Industry Co., Ltd., Tokyo, Japan, printed Jan. 1996.
Furlan, M. et al., "Triplet structure of von Willebrand factor reflects proteolytic degradation of high molecular weight multimer," Proc. Natl. Acad. Sci., vol. 90, Aug. 1993, pp. 7503-7507.
De Romeuf, C. et al., "Heparin binding assay of von Willebrand factor (vWF) in plasma milieu—evidence of the importance of the multimerization degree of vWF," (Abstract).

* cited by examiner

*Primary Examiner*—Jon Weber
*Assistant Examiner*—Abdel A. Mohamed
(74) *Attorney, Agent, or Firm*—Foley & Lardner LLP

(57) ABSTRACT

Method for preparing a factor VIII solution that is essentially free of viruses and essentially devoid of vWF (von Willebrand factor) and factor VIII-vWF complexes by (a) obtaining a starting factor VIII solution devoid of factor VIII-vWF complexes; and (b) filtering the solution through a hydrophilic virus filter.

13 Claims, 1 Drawing Sheet

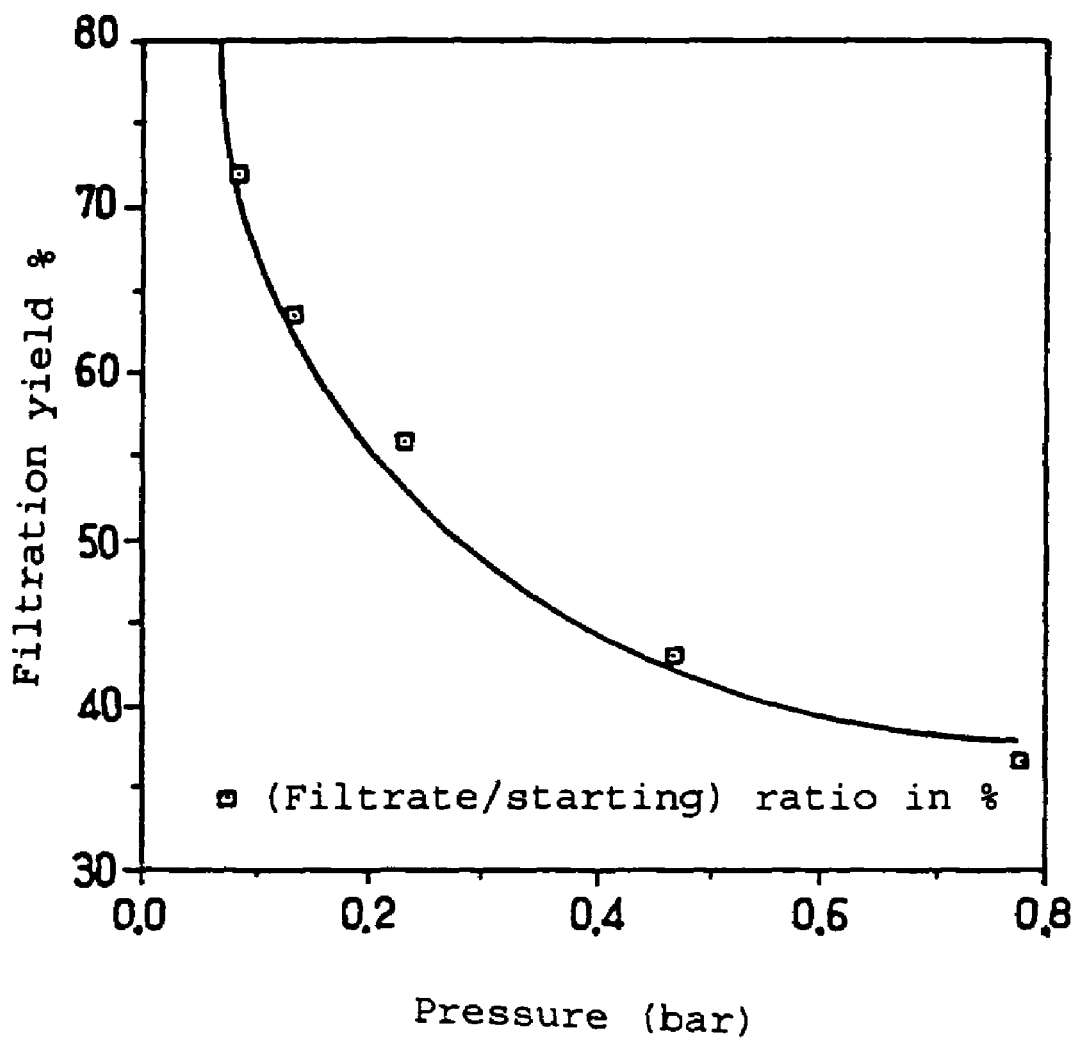
FIG_1

METHOD OF FILTERING VIRUSES FROM A FACTOR VIII SOLUTION

BACKGROUND OF THE INVENTION

The present invention concerns a method for preparing, by filtration, a factor VIII solution which is virally secure and essentially devoid of high molecular weight von Willebrand factor (vWF) from a highly or very highly pure factor VIII solution which contains or is essentially devoid of high molecular weight factor VIII-vWF complexes.

SUMMARY OF THE INVENTION

Factor VIII is a protein component of the blood which for many years has been used for treating individuals suffering from hemophilia A, which is a congenital disease caused by a deficiency or an absence of factor VIII in the blood. For a long time, factor VIII-enriched plasmatic concentrates were used for treating the patients.

The most commonly used concentrates were the cryoprecipitate and the purified concentrates obtained from the cryoprecipitate. Usually, the term cryoprecipitate refers to a precipitate obtained from a frozen human plasma by a low temperature plasmatic fractionation technique. The frozen plasma is softened at a temperature of approximately −5° C. to −15° C., and then slowly reheated with stirring to a temperature which does not exceed 3° C. Under these conditions, the frozen plasma partially melts to give a liquid phase and a solid phase, the solid phase then being recovered by centrifugation to give the cryoprecipitate, which should then be purified to obtain sufficiently pure factor VIII preparations. This cryoprecipitated fraction is composed essentially of fibrinogen, fibronectin, factor VIII and von Willebrand factor (vWF).

In this cryoprecipitated fraction, the factor VIII is generally associated with vWF, which stabilizes the factor VIII by complexation.

For a long time, the purification steps were essentially directed toward separating, from the factor VIII, unwanted proteins such as, in particular fibrinogen and fibronectin.

However, it is now known that one of the essential problems linked to the preparation of factor VIII from plasma lies in the necessity to inactivate/remove, with satisfactory yields, viruses originally contained in the blood.

Although it is difficult to establish an exhaustive list of these viruses, mention may be made in particular of the various hepatic viruses, hepatitis A, hepatitis B, hepatitis C and hepatitis G, or the various forms of the AIDS virus (HIV).

Many viral inactivation techniques have thus been developed, such as heating to dryness, pasteurization or solvent/detergent treatment. This set of techniques is relatively effective with respect to enveloped viruses, but the inactivation or removal of naked viruses, in particular small viruses such as the B19 parvovirus or the hepatitis A virus, remains one of the major problems.

More recent technology uses the viral retention capacities of small-pore-size membranes. This technology in fact exhibits notable effectiveness with respect to viruses of small size such as the B19 parvoviruses or the hepatitis A virus, and can be applied to low molecular weight proteins. However, the cutoff thresholds used, which are lower than 900 kD, do not make it possible to envisage the filtration of high molecular weight proteins or protein complexes such as factor VIII without major loss of yield.

Thus, for example, patent publication WO 96/00237 describes a method for improving the filterability of proteins in a solution containing at least one macromolecule, which consists in using a solution in which the total salt content varies from 0.2 M to saturation of the solution with the salt concerned. The effect of this high salt content is to increase the filtration yields. Preferably, the filtration step is used at a stage at which the specific activity of the macromolecule of interest is already very high, so that it is possible to use a filter with very fine structure and to remove very small viruses.

However, this document does not in any way envisage the filtration of solutions containing very high molecular weight molecules such as factor VIII, and in particular factor VIII of plasmatic origin, which is generally associated with vWF, thus forming high molecular weight complexes. This document cites the example of a deleted form of recombinant factor VIII which has an average molecular weight of about 170 kD, and is totally devoid of vWF. All the examples relate to factor IX, the average molecular weight of which is about 55 kD, and this document emphasizes that the method described is particularly suited to this size of molecule, the cutoff threshold of the filter moreover having to be slightly higher than the size of the molecule to be filtered. Thus, for factor IX, the filter used has a cutoff threshold of 70 kD.

So, as indicated above, factor VIII, according to its origin, can be in a complexed form which gives it a significant size, this size being able to reach 20,000 kD in terms of molecular weight and several tens of nanometers in terms of particle size (>106 nm for the main axis of the molecule, Eppel et al., Langmuir 1993, 9, 2281–88, American Chemical Society). No means is currently available for satisfactorily filtering this type of molecule and simultaneously removing viruses of small size such as for example the B19 parvoviruses which have a size of about 18 to 20 nm.

DETAILED DESCRIPTION OF THE INVENTION

The inventors have now found, surprisingly, that it is possible to obtain, by filtration, a factor VIII solution which is virally secure and essentially devoid of high molecular weight vWF from a solution containing highly or very highly pure factor VIII, which contains or is essentially devoid of high molecular weight factor VIII-vWF complexes.

For this reason, a subject of the invention is a method for preparing, by filtration, a factor VIII solution which is virally secure and essentially devoid of high molecular weight vWF, according to which:
  a solution containing highly or very highly pure factor VIII is prepared, which contains or is essentially devoid of high molecular weight factor VIII-vWF complexes;
  a step a) is optionally carried out, which enables, if required, the dissociation of the high molecular weight factor VIII-vWF complexes and the production of a solution which is essentially devoid of high molecular weight vWF-associated factor VIII;
  a step b) is carried out, of filtration of said solution which is essentially devoid of high molecular weight vWF-associated factor VIII through a hydrophilic filter having a porosity as low as 15 nm.

The preparation by filtration of an FVIII solution advantageously makes it possible to produce a solution which is essentially devoid of high molecular weight vWF, in particular of vWF having a degree of polymerization greater than or equal to 15, i.e. in which the vWF is both qualitatively and quantitatively controlled. The method according to the invention also makes it possible to significantly increase the filtration yields, due to the decrease in the amount of high molecular weight protein complexes, and to produce a solution having a satisfactory degree of purity, while at the same time ensuring the viral removal of human pathogenic viruses of size $\geq 15$ nm.

Step a), which enables the dissociation of a high molecular weight factor VIII-vWF complex, may or may not be required depending on the origin and the method of preparation of the starting factor VIII solution, which condition the presence or absence of high molecular weight vWF-associated factor VIII in the starting solution.

The dissociation of the FVIII-vWF complex is obtained by means of at least one chaotropic ion present in sufficient amount to enable the dissociation. Any ion known to have chaotropic activity can be used.

They will be preferably divalent ions introduced into the factor VIII solution in the form of a saline solution from 0.2 M to salt saturation.

By way of non-limiting examples, mention may be made of $CaCl_2$ or $MgCl_2$. A $CaCl_2$ solution will preferably be used. The concentration of the solution will be preferably approximately 0.35 M.

It has been observed that, besides the conditions specific to the filtration, the conditions used for the dissociation have an influence on the subsequent filtration yield. The parameters which define this set of conditions are, during the dissociation step, the nature of the salts and their concentration, and during the filtration step, the pressure and the temperature.

Surprisingly, the filtration yields are considerably improved when the transmembrane pressure during the filtration is lowered to very low values, below the recommendation thresholds recommended by the filter supplier.

The temperature also exerts a not inconsiderable influence on the filtration yields, the effect of temperature values which are too low or too high being to increase the number of multimeric forms of the vWF. Advantageously, a temperature of about 35±5° C. will be chosen.

Among the virus filters available on the market or under development, mention may be made of, for example, the PLANOVA® 15N membrane sold by the company Asahi Chemical Industry. PLANOVA® 15N is a fiberous filter having a mean pore size of 15±2 nm.

In this case, the filter is used preferably at a pressure lower than 0.3 bar, advantageously lower than 0.2 bar.

Various filtration techniques can be used. The most common techniques are the tangential filtration or frontal filtration techniques, which can be used with the same types of filter.

The starting factor VIII solution, which has been prepurified, can be prepared in various ways; for example from a plasmatic fraction such as the cryoprecipitated fraction of the plasma, or by the recombinant pathway. All the preparation conditions known to persons skilled in the art can be used. In a non-limiting manner, mention may be made of the following purification methods which enable the production of a prepurified factor VIII solution which can be used for implementing the method according to the invention:

Ion exchange chromatography, for example according to one of the variants described in patents EP-B-359 593, EP 0 343 275, U.S. Pat. No. 4,743,680, WO 97/17370 and EP 0 173 242.

Immunoaffinity chromatography, for example according to one of the variants described in the patent application publications WO 97/39033 or EP 0 286 323, or in the document Zimmerman and Fulcher, Thrombosis Res., Suppl. VII, p 58, 1987; Berntorp and Nilson, Thrombosis Res., Suppl. VII, p 60, 1987.

Gel filtration chromatography in dissociating or nondissociating medium as described by P. J. Fay (P. J. Fay et al. Proc. Nat. Acad. Sci. USA Vol. 79 p 7200–7204, 1982).

Affinity chromatography on immobilized heparin as described in patent application publication WO 93/22337.

Typically, the purification by ion exchange chromatography from a plasmatic fraction such as the cryoprecipitated fraction of the plasma comprises a viral inactivation step which enables the inactivation of enveloped viruses. Various chromatographic systems can be used, the conditions of adsorption then elution of the factor VIII-concentrated fraction then possibly having an influence on the subsequent yields of the method. The nature of the matrix and of the ion exchanger can be varied. A weak ion exchange chromatographic system, such as for example Toso Haas Toyopearl-DEAE 650 M gel, or a strong ion exchange chromatographic system, such as for example Q-Sepharose Fast Flow gel (Pharmacia Biotech), can thus be used. When the starting solution is prepared by ion exchange purification, it contains a significant amount of high molecular weight vWF-associated factor VIII, and step a) is essential.

The dissociation in step a) can be carried out at the same time as the elution or, according to another aspect, after the elution. The effect of an elution carried out in the presence of a chaotropic salt is to increase the elution yield with respect to an elution carried out in the presence of a salt such as NaCl, while at the same time ensuring the dissociation which is essential for performing the subsequent filtration step under the required conditions.

According to a preferred embodiment, the factor VIII concentrated solution obtained at the end of the purification by ion exchange chromatography is thus eluted under the dissociating conditions of step a), i.e. in the presence of a chaotropic ion.

The prepurification of the starting factor VIII solution can also be obtained by a heparin precipitation technique. In this case, a cryoprecipitated fraction of the plasma is adsorbed for example onto an aluminum hydroxide gel, in the presence of heparin, with cooling to a temperature from approximately 14° C. to approximately 19° C. and centrifugation; A first viral inactivation step, carried out on the precipitation supernatant, can be carried out advantageously by a solvent/detergent treatment as described in European patent publication EP-A-0343275. The pH and osmolality of the precipitation supernatant are then adjusted before the ion exchange chromatography step.

According to another embodiment, the starting factor VIII solution is obtained by immunoaffinity. In this case, the starting solution may be essentially devoid of high molecular weight vWF-associated factor VIII. The use of step a) which enables the dissociation of the high molecular weight factor VIII-vWF complex is then optional.

Finally, it can also be envisaged to start from a solution of recombinant factor VIII, which may require an additional viral inactivation step. It will not be necessary to use step a).

Preferably, the starting factor VIII solution will have a specific activity at least equal to 50 IU/mg, preferably at least equal to 100 IU/mg, the filterability of the solution increasing with the specific activity of the factor VIII.

The specific activity as indicated is intended to indicate that before optional addition of albumin with a view to stabilizing the factor VIII.

More particularly, a starting solution will be used in which the factor VIII concentration: C is from approximately 2 to approximately 100 U/ml, preferably from approximately 10 to approximately 50 U/ml.

The protein content of the starting factor VIII solution will be advantageously from approximately 0.05 to approximately 0.5 mg/ml, preferably from approximately 0.1 to approximately 0.5 mg/ml.

The protein content is determined by the Bradford protein assay technique (assay kit sold by the company Pierce).

Once the filtration has been carried out, the factor VIII and von Willebrand factor which have been filtered are reassociated in the form of complexes, after removal of the dissociating agents, for example by dialysis, and the factor VIII solution formulated for commercial use is recovered, optionally after a freeze-drying step.

A subject of the invention is also a factor VIII solution which is virally secure, which is essentially devoid of high molecular weight vWF, and which is capable of being obtained by the method according to the invention.

Finally, the invention concerns the solutions obtained according to the invention as medicinal products, more particularly for treating hemophilia A.

The invention will be described in more detail with the aid of the following examples, which illustrate the invention without however limiting the scope thereof. The examples are accompanied by FIG. 1 which represents:

FIG. 1: curve which demonstrates the variation of the filterability of the factor VIII on Planova® 15 N membrane as a function of the pressure applied to the system. The pressure, expressed in bar, is shown on the x-axis and the filtration yield, expressed as a percentage (ratio between the FVIIIC activity expressed in IU/ml of the filtrate and that of the starting product) is shown on the y-axis.

EXAMPLE 1

Preparation of a factor VIII solution, by filtration, from a cryoprecipitated fraction of plasma.

The preparation of the starting factor VIII solution is carried out in accordance with the teaching of patent FR 2 632 309, the content of which is incorporated herein by way of reference.

835 g of cryoprecipitate, representing 113.5 liters of plasma, are redissolved in a solution of heparinized water (3 IU/ml) by stirring at room temperature for 30 minutes. 4217 ml of solution rich in factor VIII and in proteins are clarified by adsorption onto 90 g of aluminum hydroxide gel and by acid precipitation (pH 6.50) and lowering of the temperature to between 15 and 19° C. A fibrinogen- and fibronectin-enriched precipitate is separated by centrifugation, which makes it possible to obtain a clear solution of factor VIII of intermediate purity which is inactivated for enveloped viruses by addition of Polysorbate 80 and of tri-n-butyl phosphate (respectively in solution q.s. 1% and 0.3%) for at least 6 hours at pH 7.1.

5172 ml of factor VIII solution which has been virus-inactivated with respect to enveloped viruses are adsorbed onto 560 ml of weak anion exchange chromatography gel (TosoHaas Toyopearl-DEAE 650M) which has been pre-equilibrated in buffered saline solution. After 2 hours of adsorption, the gel is washed with a saline solution which has an osmolality of 390 mOsm/kg, and which is buffered to pH 7.00. The fraction which is not adsorbed onto the gel is rich in fibrinogen. The gel is then eluted from the von Willebrand factor-enriched fraction by increasing the osmolality to 452 mOsm/kg. The fraction which is concentrated in and very highly pure for factor VIII is then eluted by modifying the pH to 6.0 and increasing the ionic strength. The eluted fraction is then $CaCl_2$-adjusted to a concentration of 0.35 M and an osmolality of 1300±100 mOsm/kg. This fraction consists of a mixture of factor VIII and von Willebrand factor in a dissociated form due to the action of the high calcium content.

1260 ml of a solution which is stable at +4° C. are extemporaneously reheated to +35° C. to undergo a step of virus removal by filtration using a BMM PLANOVA® 15N filter having a 15-nanometer porosity threshold and a surface area of 0.12 m². During the filtration, the flow rate is maintained in such a way that the transmembrane pressure is always lower than 0.2 bar. After filtration of the factor VIII, 210 ml of buffered saline solution of osmolality 1300 mOsm/kg are then filtered through the membrane to recover 1470 ml of factor VIII solution free of pathogenic viruses. The buffer solution makes it possible to equilibrate the filters for osmolality and pH, and is used to rinse the filters after filtration of the factor VIII. The factor VIII solution obtained is impoverished in von Willebrand factor of a very high degree of polymerization ($\geqq 15$), but contains sufficient von Willebrand factor of a degree of polymerization $\geqq 5$ and $\geqq 10$ to recomplex the factor VIII after dialysis.

Results:

Table 1 indicates, at the various steps of the method according to the invention, the amounts of factor VIII obtained, as well as the specific activity (SA), the protein content and the yield from the step in question.

TABLE 1

|  | Volume (ml) | FVIII:C (IU/ml) | Proteins mg/ml | FVIII total (IU) | SA (IU/mg) | Yield (%) |
|---|---|---|---|---|---|---|
| Eluted solution from chromatography | 1260 | 22 | 0.32 | 27720 | 69 | 100 |
| Factor VIII solution filtered at 15 nm | 1470 | 12 | 0.14 | 17640 | 86 | 64 |
| Solution dialyzed and concentrated | 149 | 108 | 1.13 | 16092 | 95 | 58.1 |

EXAMPLE 2

The conditions are identical to those of Example 1 except that 10,000 g of cryoprecipitate, representing 1330 liters of plasma, are used. 13,700 ml of factor VIII solution virus-inactivated with respect to envelope viruses are filtered. After filtration of the factor VIII, 2 liters of buffer solution, of osmolality 1300 mOsm/kg are filtered to recover 15,700 ml of factor VIII solution free of pathogenic viruses. The filtration membrane used is a BMM PLANOVA® 15N membrane with a surface area of 1.0 m².

Table 2 reproduced below indicates, for a filtration of an equivalent 1330 liters of plasma through BMM PLANOVA® 15N membrane with a surface area of 1.0 m², the amounts of factor VIII obtained at the various steps of the filtration method, as well as the specific activity and the yield from the step in question.

TABLE 2

|  | Volume (ml) | FVIII:C (IU/ml) | Proteins mg/ml | FVIII total (IU) | SA (IU/mg) | Yield (%) |
|---|---|---|---|---|---|---|
| Eluted solution from chromatography | 13700 | 15.0 | 0.09 | 205500 | 167 | 100 |
| Factor VIII solution filtered at 15 nm | 15700 | 7.9 | 0.045 | 124030 | 176 | 60.3 |
| Solution dialyzed and concentrated | 956 | 119 | 0.72 | 113764 | 165 | 55.5 |

TABLE 3

|  | Volume (ml) | FVIII:C (IU/ml) | FVIII total (IU) | Proteins mg/ml | SA (IU/mg) | Yield (%) |
|---|---|---|---|---|---|---|
| Eluted solution from chromatography | 1280 | 19 | 24320 | 0.20 | 95 | 100 |
| Factor VIII solution filtered at 15 nm | 1460 | 13 | 18980 | 0.12 | 108 | 78 |
| Solution dialyzed and concentrated | 164 | 92 | 15088 | 0.95 | 97 | 62 |

EXAMPLE 3

Preparation of a factor VIII solution, by filtration, from a fraction which is derived from a cryoprecipitate of plasma, and which is prepurified by heparin precipitation.

The preparation of the starting factor VIII solution is carried out in accordance with the teaching of U.S. Pat. No. 4,743,680, the content of which is incorporated by way of reference.

678 g of cryoprecipitate, representing 92.2 liters of plasma, are redissolved in a solution of heparinized water (3 IU/ml) by stirring at room temperature for 30 minutes. 3424 ml of solution rich in factor VIII and in proteins are clarified as in Example 1.

4200 ml of factor VIII solution which has been virus-inactivated with respect to envelope viruses under the same conditions as Example 1 are adsorbed, after acidification at pH 6.50, onto 300 ml of strong anion exchange chromatography gel (Pharmacia Biotech Q-Sephar⊖se Fast Flow) which has been preequilibrated in buffered saline solution. After 2 hours 30 minutes of adsorption, the gel is washed with a saline solution which has an osmolality of 450 mOsm/kg, and which is buffered at pH 6.50. The fraction which is not adsorbed onto the gel is rich in fibrinogen. The gel is then eluted from the von Willebrand factor-enriched fraction by increasing the osmolality to 581 mOsm/kg. The fraction which is concentrated in and very highly pure for factor VIII is then eluted by modifying the pH to 6.0 and increasing the ionic strength. The eluted fraction is then $CaCl_2$-adjusted to a concentration of 0.35 M and an osmolality of 1300±100 mOsm/kg. This fraction consists of a mixture of factor VIII and von Willebrand factor in a dissociated form due to the action of the high calcium content.

1280 ml of a solution which is stable at +4° C. are extemporaneously reheated to +35° C. to undergo a step of virus removal by filtration, in the same way as in Example 1, through a Planova 15N membrane having a 15-nanometer porosity threshold and a surface area of 0.12 m². A volume of 180 ml of buffer solution of osmolality 1300 mOsm/kg is then filtered to recover 1460 ml of factor VIII solution free of pathogenic viruses. This factor VIII solution is depleted in von Willebrand factor of a very high degree of polymerization ($\geq 15$), but contains sufficient von Willebrand factor of a degree of polymerization $\geq 5$ and $\geq 10$ to recomplex the factor VIII after dialysis.

Results:

Table 3 reproduced below indicates, at the various steps of the filtration method, the amounts of factor VIII obtained, the total amount of protein, as well as the specific activity (SA) and the yield from the step in question.

EXAMPLE 4

Variation of the filterability of a factor VIII solution through a PLANOVA® 15 N membrane as a function of the nature and of the concentration of the salts used for the dissociation.

Results:

Table 4 reproduced below demonstrates the variations in the filtration yield as a function of these various parameters, the other operating conditions of the method remaining those defined in Example 1.

TABLE 4

| Dissociating agent (M) | Filtration yield (%) |
|---|---|
| 0.35 M $CaCl_2$ | 45 |
| 0.35 M NaCl | 10 |
| 1.0 M NaCl | 26 |

The use of dissociating agents makes it possible to significantly increase the filterability of the factor VIII. The removal of these agents by dialysis after filtration induces a reassociation of the factor VIII-von Willebrand factor complexes. The analysis of the products obtained demonstrates a good capacity of the von Willebrand factor to bind the factor VIII.

EXAMPLE 5

Variation of the filterability of a factor VIII solution through a PLANOVA® 15 N membrane as a function of temperature and pressure parameters.

Table 5 reproduced below indicates the filtration yield obtained by varying the pressure and the temperature, the salt used for the dissociation and its concentration remaining unchanged. For a given pressure, when the temperature is lowered, a significant decrease in the filtration yield is observed.

FIG. 1 also clearly demonstrates that lowering the transmembrane pressure to very low values allows considerable improvement in the yield.

TABLE 5

| Dissociating agent | Pressure (bar) | Temperature (° C.) | Filtration yield (%) |
|---|---|---|---|
| 0.35 M $CaCl_2$ | $\leq 0.10$ | 35 ± 2 | 70 |
| 0.35 M $CaCl_2$ | $\leq 0.20$ | 35 ± 2 | 58 |

TABLE 5-continued

| Dissociating agent | Pressure (bar) | Temperature (° C.) | Filtration yield (%) |
|---|---|---|---|
| 0.35 M $CaCl_2$ | 0.50 | 35 ± 2 | 45 |
| 0.35 M $CaCl_2$ | ≦0.20 | 20 ± 2 | 42 |

EXAMPLE 6

Study of the viral retention capacity of the filtration system under the filtration conditions of Example 1.

The phage øx174, the size of which can be evaluated at 25–30 nm, is used as a viral model. The membrane and the operating conditions are those described in Examples 1 and 2.

Results:

The results contained in Table 6 below demonstrate an entirely satisfactory viral retention capacity.

TABLE 6

| | Filtration surface area ($m^2$) | FVIII:C (IU/ml) | Volume filtered ($l/m^2$) | Viral load (log) | Viral retention (log) |
|---|---|---|---|---|---|
| Example 1 | 0.01 | 15 | 14 | 8.3 | >6.8 |
| Example 2 | 0.01 | 19 | 15 | 7.5 | >7.0 |

EXAMPLE 7

Effect of the method according to the invention on the vWF content in the factor VIII solution.

The vWF content and the vWF multimer profile were compared in a factor VIII solution as described in Example 1, before and after using the method according to the invention.

The results obtained are reported in Table 7 below.

TABLE 7

| | Before filtration | After filtration |
|---|---|---|
| FVIII (IU/ml) | 17 | 7.9 |
| vWF (IU/ml) | 5.6 | 0.39 |
| vWF/FVIII | 0.33 | 0.05 |
| wWF multimers ≧15 | 12% | — |
| vWF multimers ≧10 | 32.4% | 3.3% |
| vWF multimers ≧5 | 71.5% | 35.6 |

Thus, using the method according to the invention indeed makes it possible to obtain a factor VIII solution which is essentially devoid of high molecular weight vWF, in particular which is essentially devoid of the multimeric formulae with a degree of polymerization ≧15.

What is claimed is:

1. A method for preparing a factor VIII solution comprising:
   (a) obtaining a starting factor VIII solution comprising factor VIII-von Willebrand factor (factor VIII-vWF) complexes; and
   (b) filtering said solution through a hydrophilic virus filter, wherein the virus filter has a mean pore size of 13 to 17 nm and
   wherein the filtering occurs in the presence of $CaCl_2$ ions, at a pressure of less than 0.3 bar and a temperature of about 35±5° C.; and
   wherein the filtered solution is free of viruses and devoid of high molecular forms of vWF and factor VIII-vWF complexes.

2. The method according to claim 1, wherein the $CaCl_2$ is present in the solution from 0.2 M to saturation.

3. The method according to claim 1, wherein the starting factor VIII solution is treated with an effective amount of an anti-viral solvent, a detergent, or both.

4. The method according to claim 1, wherein the starting factor VIII solution is immunopurified.

5. The method according to claim 1, wherein the starting factor VIII solution comprises recombinantly produced factor VIII.

6. The method according to claim 1, wherein the starting factor VIII solution of (a) is derived from a cryoprecipitated fraction of plasma.

7. The method according to claim 6, wherein the starting factor VIII solution is obtained by a further heparin precipitation.

8. The method according to claim 1, wherein the $CaCl_2$ is present in the solution from 0.35 M to saturation.

9. The method according to claim 8, wherein the filter has a pore size of 15 nanometers.

10. The method according to claim 8, wherein the filter is used at a pressure lower than 0.2 bar.

11. The method according to claim 1, further comprising dissociating factor VIII-vWF complexes of the starting solution prior to (b) filtering.

12. The method according to claim 11, wherein the factor VIII-vWF complexes of the starting factor VIII solution are dissociated by ion exchange chromatography.

13. The method according to claim 12, wherein the starting factor VIII solution of (a) is derived from a cryoprecipitated fraction of plasma.

* * * * *